United States Patent [19]

Knox

[11] Patent Number: 5,049,273

[45] Date of Patent: Sep. 17, 1991

[54] SUCTION STRAINING APPARATUS

[76] Inventor: Sheree N. Knox, 1729 Hailey Apt. E56, Sweetwater, Tex. 79556

[21] Appl. No.: 594,443

[22] Filed: Oct. 5, 1990

[51] Int. Cl.[5] .......................... B01D 35/00; A61M 1/00
[52] U.S. Cl. ..................................... 210/406; 210/443;
604/4; 604/5; 604/319; 604/406
[58] Field of Search ............... 210/443, 429, 444, 237,
210/797, 237, 406, 454, 432, 475, 448, 384, 415,
407, 416.1, 94, 402; 15/320; 250/390.1; 55/335;
604/212, 4, 5, 319, 406

[56] References Cited

U.S. PATENT DOCUMENTS

| | | | |
|---|---|---|---|
| 2,558,987 | 11/1948 | Shaw | 604/406 |
| 3,747,770 | 7/1973 | Zentis | 210/402 |
| 3,782,414 | 1/1974 | Holbrook | 604/319 |
| 4,419,093 | 11/1983 | Deaton | 604/319 |
| 4,460,361 | 7/1984 | Nichols | 604/319 |
| 4,559,034 | 12/1985 | Kirita et al. | 604/5 |

Primary Examiner—Robert A. Dawson
Assistant Examiner—Ana Fortuna
Attorney, Agent, or Firm—Leon Gilden

[57] ABSTRACT

An organization particularly for use in medical environments, wherein an inlet port is operatively coupled with a vacuum canister, wherein the inlet port includes a coupling member mounting a replaceable and removable straining device mounted the coupling member to effect straining of various bodily fluids directed within the container.

3 Claims, 2 Drawing Sheets

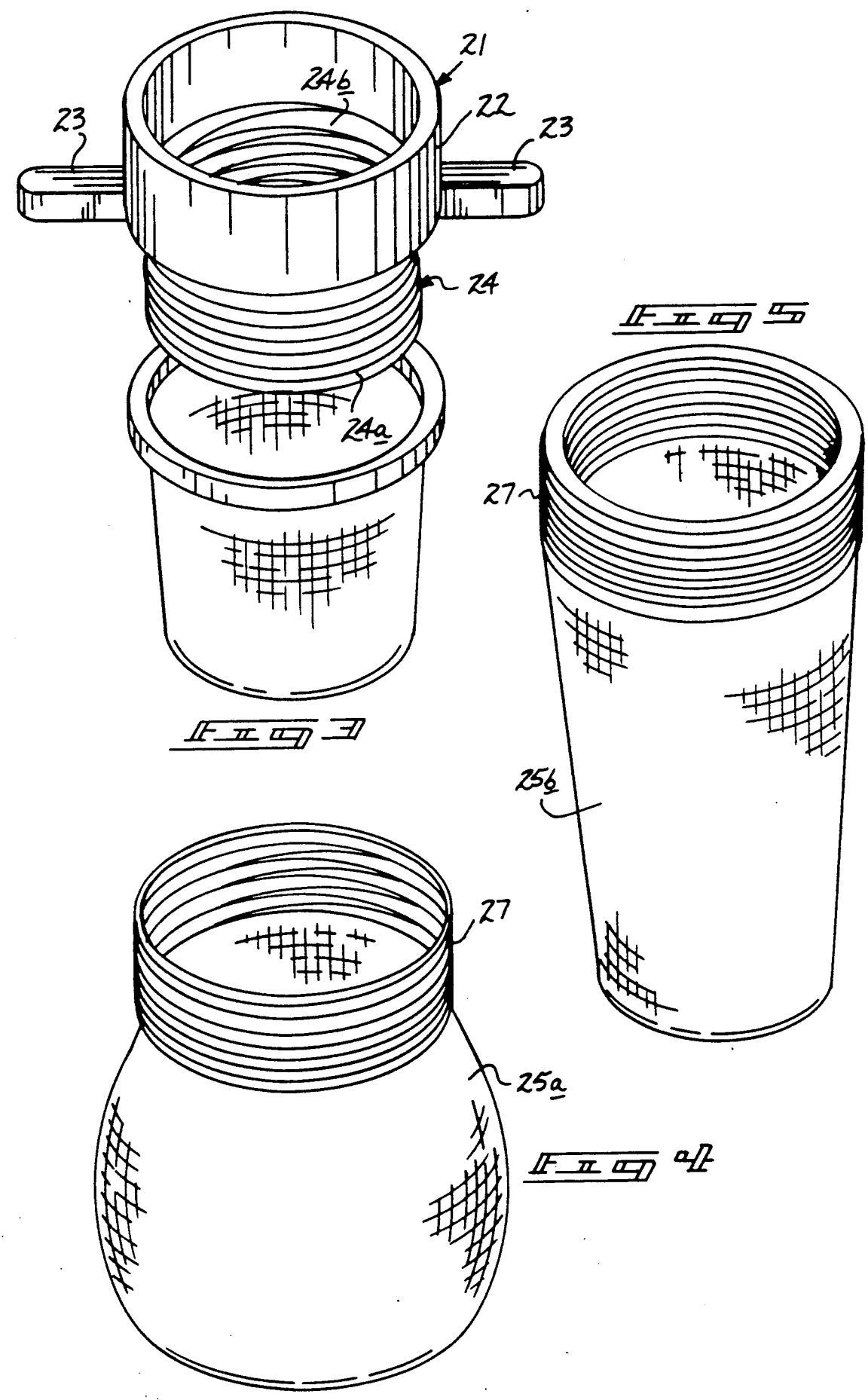

SUCTION STRAINING APPARATUS

BACKGROUND OF THE INVENTION

1. Field of the Invention

The field of invention relates to suction devices, and more particularly pertains to a new and improved suction straining apparatus wherein the same permits replacement and reuse of a straining basket in cooperation with the apparatus.

2. Description of the Prior Art

Vacuum devices of various sorts have been utilized in the prior art, and typically in use with a filtration bag. The instant invention sets forth an organization for use in straining of various solid components and particulates from bodily fluids, particularly in a suctioning apparatus of bodily fluids that are utilized for examination and reintroduction of such fluids within a patient.

Suction canisters of various types as set forth in the prior art may be found in U.S. Pat. No. 3,873,285 to Allen; U.S. Pat. No. 2,789,661 to Brace; U.S. Pat. No. 3,564,641 to Meyer; U.S. Pat. No. 2,958,893 to Carlberg, et al.; and U.S. Pat. No. 4,010,015 to Brown setting forth conventional vacuum canister organizations.

As such, it may be appreciated that there continues to be a need for a new and improved suction straining apparatus which addresses both the problems of ease of use as well as effectiveness in construction in the selective straining of bodily fluids and in this respect, the present invention substantially fulfills this need.

SUMMARY OF THE INVENTION

In view of the foregoing disadvantages inherent in the known types of suction apparatus now present in the prior art, the present invention provides a suction straining apparatus wherein the same utilizes a replaceable filtration basket mounted underlying an intake port of a suction canister organization. As such, the general purpose of the present invention, which will be described subsequently in greater detail, is to provide a new and improved suction straining apparatus which has all the advantages of the prior art suction apparatus and none of the disadvantages.

To attain this, the present invention provides an organization particularly for use in medical environments, wherein an inlet port is operatively coupled with a vacuum canister, wherein the inlet port includes a coupling member mounting a replaceable and removable straining device mounted the coupling member to effect straining of various bodily fluids directed within the container.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved suction straining apparatus which has all the advantages of the prior art suction apparatus and none of the disadvantages.

It is another object of the present invention to provide a new and improved suction straining apparatus which may be easily and efficiently manufactured and marketed.

It is a further object of the present invention to provide a new and improved suction straining apparatus which is of a durable and reliable construction.

An even further object of the present invention is to provide a new and improved suction straining apparatus which is susceptible of a low cost of manufacture with regard to both materials and labor, and which accordingly is then susceptible of low prices of sale to the consuming public, thereby making such suction straining apparatus economically available to the buying public.

Still yet another object of the present invention is to provide a new and improved suction straining apparatus which provides in the apparatuses and methods of the prior art some of the advantages thereof, while simultaneously overcoming some of the disadvantages normally associated therewith.

Still another object of the present invention is to provide a new and improved suction straining apparatus wherein the same permits selective mounting, replacement, and maintenance of a suction straining basket relative to a fluid straining apparatus.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an isometric illustration of a mounting collar mounting the straining basket.

FIG. 4 is an isometric illustration of a further straining basket utilized by the instant invention.

FIG. 5 is an isometric illustration of a yet further straining basket utilized by the instant invention.

DESCRIPTION OF THE PREFERRED EMBODIMENT

Figure 1:
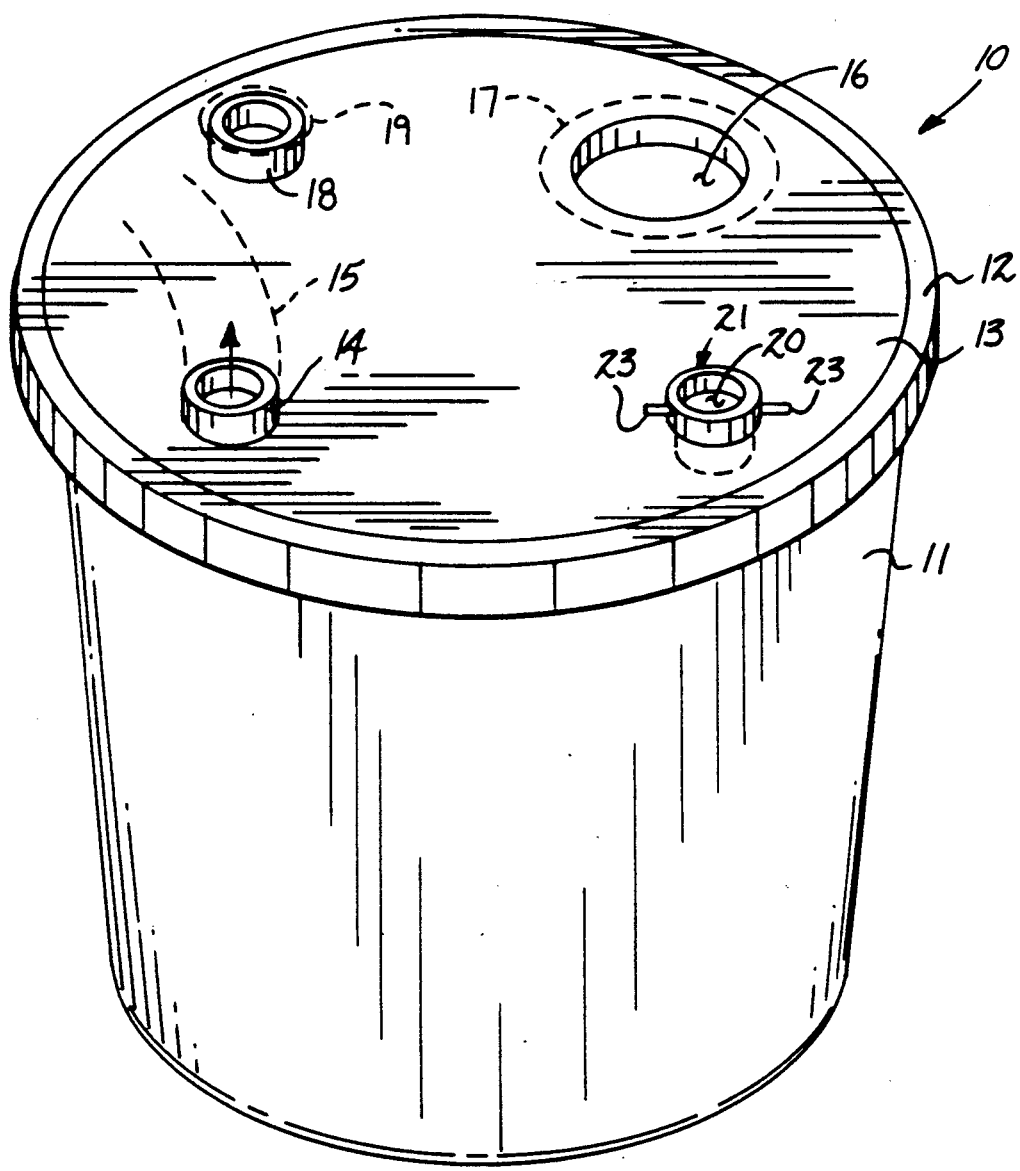
FIG. 1 is an isometric illustration of the instant invention.
Figure 2:
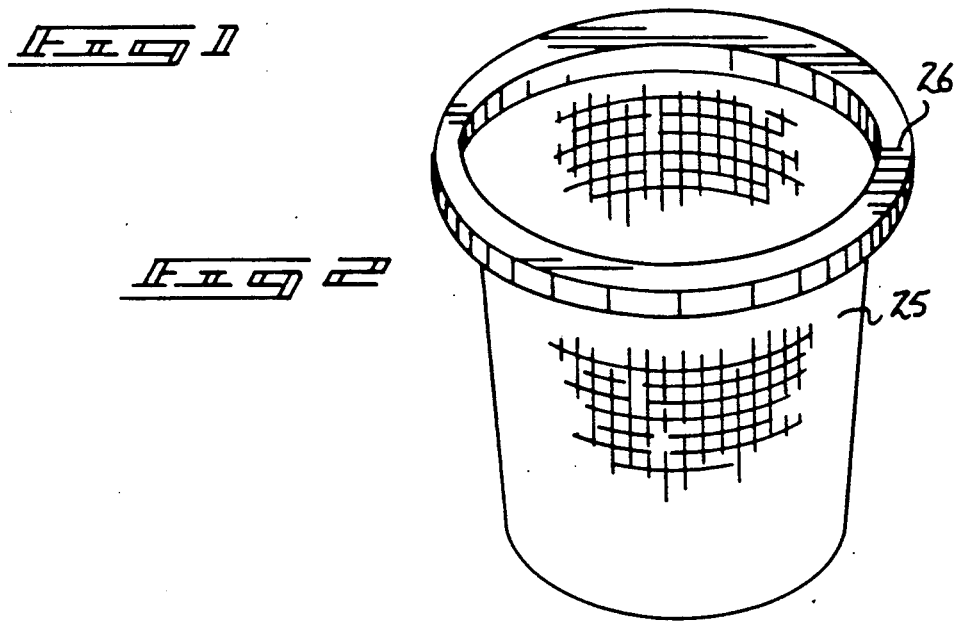
FIG. 2 is an isometric illustration of a basket utilized by the instant invention.

With reference now to the drawings, and in particular to FIGS. 1 to 5 thereof, a new and improved suction straining apparatus embodying the principles and concepts of the present invention and generally designated by the reference numeral 10 will be described.

More specifically, the suction straining apparatus 10 of the instant invention includes a container 11, with a lid 12 removably mounted thereon, wherein the lid may be mounted by use of friction or threaded interconnection, as is conventional in the prior art. The lid 12 includes a central web 13, with a vacuum port 14 and an associated vacuum hose 15 selectively mounted thereto to effect a vacuum within the container 11. A contents discharge port 16 is also provided, with a discharge port cover lid 17 removably mounted for use in permitting discharge of remaining fluids contained within the container 11 subsequent to use. Subsequent to use, a secondary port 18 is provided, also with a secondary port removal cover and lid 19. The secondary port may also be utilized to secure a further vacuum source thereto to enhance vacuum within the container 11 as a mode of use of the secondary port 18.

An internally threaded intake port 20 of a predetermined diameter includes a collar member 21 mounted thereto. The collar member 21 (see FIG. 3) includes an upper cylindrical connecting collar 22, with a plurality of diametrically mounted handles 23 mounted to the collar to enhance ease of securement of the collar member 21 to the intake port 20. The collar member 21 further includes a lower externally and internally threaded cylindrical collar 24 that is coaxially aligned with the upper cylindrical connection collar 22. A mesh straining basket 25 of a generally flexible construction includes an annular resilient clamping ring 26 that may be mounted to the lower cylindrical collar 24. Further, a first and second modified straining basket construction, as illustrated in FIGS. 4 and 5, of a generally respective convex or truncated conical construction, is provided, whereupon the externally threaded collar 24 includes external threads 24a that are threadedly engaged within the internally threaded intake port 20, wherein internal threads 24b are arranged to threadedly receive the externally threaded basket collars 27 to thereby permit unitary removal of the baskets and the collar from the central web 13, and more particularly the internally threaded intake port 20, to remove particulates and solids from fluids directed through the intake port 20.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A suction straining apparatus comprising in combination,
    a container, the container including a removable lid mounted thereon, the lid including a central web overlying the container, and
    at least one vacuum port directed through the lid for securement of a vacuum hose thereto, and
    a contents discharge port directed through the central web for discharge of fluids from the container, and
    an internally threaded intake port directed through the intake web, with straining means mounted to the intake port underlying the central web for selective removal of particulates from fluid directed through the intake port, and
    wherein the straining means includes a collar member, the collar member including an upper cylindrical connection collar mounted overlying the central web, and a coaxially aligned lower externally and internally threaded cylindrical collar, with the lower collar including external threads threadedly received within the intake port, and a strainer basket mounted to the lower collar.

2. An apparatus as set forth in claim 1 wherein the straining basket includes a flexible basket enclosure of a woven fabric mesh, with a mounting collar mounted to the basket, the mounting collar mounted to the lower collar.

3. An apparatus as set forth in claim 2 wherein the mounting collar includes an externally threaded cylindrical member, including mounting collar threads externally formed to the mounting collar, and the lower collar including internal threads, wherein the mounting collar threads are mounted to the internal threads of the lower collar for securement thereto.

* * * * *